United States Patent [19]

Wolf et al.

[11] Patent Number: 4,590,014

[45] Date of Patent: May 20, 1986

[54] SYNTHESIS OF ALKYL PHOSPHINATE SALTS

[75] Inventors: Stephen F. Wolf, St. Paul; Chung-Tsing Liu, Bloomington, both of Minn.

[73] Assignee: Economics Laboratory, Inc., St. Paul, Minn.

[21] Appl. No.: 647,918

[22] Filed: Sep. 6, 1984

[51] Int. Cl.$^4$ .................. C07F 9/38; C07C 69/34
[52] U.S. Cl. .................. 260/502.4 R; 210/699; 252/136; 560/190
[58] Field of Search ............ 260/502.4 R; 560/190

[56] References Cited

U.S. PATENT DOCUMENTS

| | | | |
|---|---|---|---|
| 2,724,718 | 11/1955 | Stiles et al. | 260/502.4 R |
| 2,957,931 | 10/1960 | Hamilton et al. | 260/502.4 R |
| 3,047,619 | 7/1962 | Brace | 260/502.4 R |
| 3,236,863 | 2/1966 | Smith et al. | 260/502.4 R |
| 3,459,808 | 8/1969 | Hall et al. | 260/606.5 |
| 3,609,075 | 9/1971 | Barbera | 252/8.6 |
| 3,812,222 | 5/1974 | Kleiner et al. | 260/502.4 R |

OTHER PUBLICATIONS

C. H. Augustin, Tenside Detergents, vol. 18, 190 (1981).
C. E. Griffin et al, J. Org. Chem., 24, 2049 (1959).
C. E. Griffin, J. Org. Chem., 25, 665 (1960).
A. R. Stiles et al, J. Amer. Chem. Soc., 74, 3282 (1952).
M. R. Kharasch et al, J. Org. Chem., 25, 1000 (1960).
A. N. Rudovik et al, Chem. Abstracts, 54, 15223f (1959).

*Primary Examiner*—J. E. Evans
*Attorney, Agent, or Firm*—Merchant, Gould, Smith, Edell, Welter & Schmidt

[57] ABSTRACT

An improved method for the preparation of alkali metal phosphinate salts by the reaction of an olefinic material with an alkali metal hypophosphite in the presence of a free radical source is disclosed.

10 Claims, No Drawings

SYNTHESIS OF ALKYL PHOSPHINATE SALTS

FIELD OF THE INVENTION

The invention relates to an improved synthesis of alkali metal phosphinates which results in high yields of active phosphinates at greatly decreased reaction times. The resultant phosphinates are highly active as detergent builders.

BACKGROUND OF THE INVENTION

Alkyl phosphinates can be prepared by the reaction of an olefin with an alkali metal salt of hypophosphorous acid. For example, the reaction of alpha-olefins with sodium hypophosphite yields sodium alkyl phosphinates when initiated photochemically or by an introduced chemical source of free radicals such as a peroxide. The reaction may be summarized as follows:

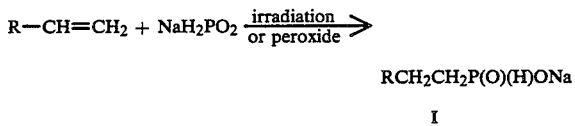

$$RCH_2CH_2P(O)(H)ONa$$

$$I$$

Alkyl phosphinate I can be converted into the corresponding phosphonate $(RCH_2CH_2P(O)(ONa)_2)$ by exposure to an oxidizing agent. Both the alkyl phosphonates and alkyl phosphinates can function as anionic surfactants, and can act to enhance the wetting power of aqueous media.

Although the alkali metal phosphinates may be useful as surfactant additives for household and industrial detergents, this potential has not been realized due to the barriers encountered to efficient, commercially-viable syntheses of this class of compounds. For example, numerous yield-reducing side reactions, including telomerization, double bond polymerization, abstraction of alkylic hydrogen atoms and hypophosphorous acid oxidation can occur. In *Tenside Detergents*, Vol. 18, 190 (1981), C. H. Agustin extensively examined reaction variables with respect to the synthesis of sodium octylphosphinate from 1-octene and sodium hypophosphite monohydrate in water/ethanol, initiated by t-butyl perbenzoate. He achieved product yields of greater than 90% by dividing the unstable initiator into two equal portions. One of them was introduced into the reaction vessel with the hypophosphite, while the second one was dissolved in the 1-octene and added gradually to the refluxing solvent system, which presumably contained preformed hypophosphite radicals. Agustin concluded that a reflux time of 45 hours was essential to obtain a product with satisfactory wetting power which was calculated to be 96% sodium octyl phosphinate. Reaction times of 12.3-15.5 hours yielded a product of low wetting power which was not further analyzed.

Due to increasing labor and energy costs, a need exists for a synthesis of alkyl phosphinates which will produce equivalent or higher yields while permitting substantially decreased reaction times.

BRIEF DESCRIPTION OF THE INVENTION

We have found that high-yield reactions of an olefinic material with a hypophosphite salt to yield a phosphinate salt can be accomplished by a process comprising simultaneously reacting the olefin, essentially all of the free radical source and the alkali metal hypophosphite in an aqueous alcoholic reaction medium. Preferably the process comprises simultaneously adding the olefinic material and essentially all of the free radical source used to initiate the reaction to a hot solution of the hypophosphite salt. In preferred embodiments of the present invention, an alcohol solution of olefinic compound and the free radical source are added to the hypophosphite in an aqueous alcoholic reaction medium. During the addition, the hypophosphite solution is maintained at a temperature at or slightly above the decomposition temperature of the free radical source.

After the addition is completed, the reaction mixture can be heated for a period of time sufficient to complete the reaction. Surprisingly, we have found that under these conditions, high yields of alkyl phosphinates can be obtained using much shorter reaction times than heretofore believed to be effective. For example, alpha-olefins can be reacted with sodium hypophosphite in the presence of organic peroxides in aqueous alcohol to yield sodium alkyl phosphinates in yields of greater than 90% employing reaction times of about 4-6 hours.

It was also surprisingly discovered that alkyl phosphinates prepared according to the present invention strongly complex alkaline earth metal ions, i.e. calcium ion, and are more effective sequestering agents than alkyl phosphonates. This result indicates that water-soluble n-alkyl phosphinates will be effective as builders and conditioners in detergent formulations, where they will function as substitutes or replacements for commonly-used sequestering agents such as citrates, hydroxy malonates, nitrilotriacetates and the like. These sequestering agents act to prevent or inhibit metal cations responsible for water hardness such as $Ca^{++}$ or $Mg^{++}$ from precipitating commonly used alkali metal builder salts and anionic surfactants.

DETAILED DESCRIPTION OF THE INVENTION

According to the method of the present invention, the olefinic starting material and the free radical initiator are simultaneously added to a hypophosphite solution. The hypophosphite solution is maintained at a temperature at or slightly above the decomposition temperature of the initiator compound. Essentially all of the initiator compound is added to the hypophosphite solution along with the olefinic component. As used herein, the term "essentially all" when used with respect to the initiator compound, or free radical source, is intended to mean that substantially all of the reaction to produce the desired product is induced by the initiator added with the olefin, e.g. that none of the initiator is added to the hypophosphite solution prior to introduction of the olefinic component. While not intending to be bound by any particular theory, it is believed that the effectiveness of the present process is at least partly due to the fact that free radicals are produced under controlled conditions, in the presence of limited amounts of the olefinic component. Detrimental excesses of olefin are thus avoided, as sufficient free radicals are continuously present, and act immediately to convert the olefin into the phosphinate product.

The Olefinic Material

The method of the invention can be used to convert a wide variety of olefinic material into the corresponding phosphinate salts. Such olefinic materials include terminal and internal aliphatic olefins, cycloalkenes, and alpha, beta-unsaturated materials such as alpha, beta-unsaturated ketones, esters and carboxylic acids. The method of the present invention is particularly useful to form n-alkyl phosphinate salts from terminal or alpha-olefins. These olefins can have from 4–30 carbon atoms in the alkyl chain. Preferably they will have 6–20 carbon atoms in the chain. Alpha-olefins having about 4 to 9 carbon atoms, ($C_4$–$C_9$-n-alkenes), are especially preferred substrates for use in the present method since the resulting n-alkyl phosphinates are water soluble and thus can be used to chelate hardness ions in aqueous systems. Cycloalkenes having from about 4–12 carbon atoms in the ring are also useful olefinic substrates for the present method. Also useful are olefinic materials in which the double bond is adjacent to a reactive functionality such as a ketone or one or more carboxylic acids or esters. For example, the double bond of a di-lower alkyl ester of maleic acid has been found to be reactive under the present reaction conditions. Although normally it is contemplated that the present method will be operated under conditions of ambient pressure, e.g. about one atmosphere, slight pressurization of the reaction vessels used in the present method may be necessary to prevent the loss of low boiling olefinic materials such as n-pentene, cyclobutene and the like.

The Hypophosphite Salt

Sodium hypophosphite, which is employed in the present method as its stable monohydrate, is the preferred hypophosphite salt for use in the present invention. When sodium hypophosphite is used as the hypophosphite salt, a sodium phosphinate will be isolated as the reaction product. Although it will generally be preferred that the present method be directed toward the preparation of sodium phosphinates due to their high water solubility, stability and low cost, for some applications the preparation of other alkali metal or alkaline earth metal phosphinates may be desirable. In such cases, other alkali metal hypophosphites such as lithium hypophosphite, potassium hypophosphite, rubidium hypophosphite, or cesium hypophosphite may be employed in the present reaction with the appropriate adjustment in the solvent system, reaction temperature and the like.

In the present method the final molar ratio of olefinic material to hypophosphite salt will fall within the range of about 1.2–0.8:1. Most preferably the molar ratio of olefinic material to hypophosphite salt will be about 1-1.

The Free Radical Initiator

In the present invention a solution of the hypophosphite salt is treated with the olefinic component in the presence of an amount of a free radical source effective to catalyze the reaction between the hypophosphite anion and the olefinic double bond. Any of the common free radical sources including organic peroxides such as benzoyl peroxide or diazo compounds such as 2,2′-azobisisobutyronitrile (AIBN) may be employed in the practice of the present invention. Organic peroxyesters are the preferred initiators. Useful commercially available peroxyesters include the alkylesters of peroxycarboxylic acids, the alkylesters of monoperoxydicarboxylic acids, the dialkylesters of diperoxydicarboxylic acids, the alkylesters of monoperoxycarbonic acids, and the alkylene diesters of peroxycarboxylic acids. Among these classes of peroxyesters the alkylesters of peroxycarboxylic acids and the alkylesters of monoperoxy dicarboxylic acids have been found to be especially preferred in the practice of the present invention. The former class of peroxyesters includes t-butyl peroctoate, t-butyl perbenzoate and t-butyl peroxyneodecanoate, while the latter class includes compounds such as t-butyl peroxymaleic acid. These compounds are commercially available from Pennwalt Chemicals, Buffalo, N.Y. The amount of any free radical initiator required to catalyze the olefin-hypophosphite reaction will vary depending upon the molecular weight of the initiator and its thermal stability. In the case of the peroxyesters, mole ratios of olefin to peroxyester of 5 to 1 or more have been found to provide acceptable reaction rates.

The Solvent System

In the practice of the present invention the solvent system can be chosen with the decomposition temperature of the reaction promoter in mind. A solution of hypophosphite is typically maintained at a constant temperature while the olefinic component and the free radical initiator are simultaneously added into the reaction vessel containing the hypophosphite solution. Preferably the hypophosphite solution will be maintained at a temperature at or slightly above the decomposition point of the free radical initiator compound. This temperature will be selected on the basis of the known decomposition temperature of the free radical initiator compound and will preferably be established by means of a refluxing azeotropic organic solvent system. The most commonly employed azeotropic solvent systems for use in the present invention are mixtures of alkanols and water. For example, mixtures of ethanol and water within the range of about 2–8 parts ethanol to each part of water can be compounded so as to reflux at temperatures of about 70°–80° C. A mixture of about 300 grams of reagent alcohol (a mixture of 95% denatured ethanol with 5% isopropyl alcohol) and 100 ml of water will reflux at a temperature of about 78° C. Other organic alcohol-water systems may be selected which will reflux at temperatures at or slightly above the decomposition points of organic peroxyesters useful to initiate the present reaction, e.g. within the range of about 50°–100° C. Other alcohols useful as the organic component of the present solvent systems include methanol, isopropanol, t-butanol and the like.

Reaction Methodology

In the practice of the present invention the hypophosphite salt is first dissolved in the organic solvent system and the solution brought to a temperature at or slightly above the decomposition point of the free radical initiator compound. The olefinic material and the free radical initiator are then slowly and simultaneously added to the heated, stirred hypophosphite solution. Preferably the olefinic component and the free radical initiator compound are dissolved in an organic solvent which is the same as or is compatible with that used to dissolve the hypophosphite salt. Most preferably the olefinic compound and the free radical initiator will be added to the hypophosphite solution in a dropwise fashion after having been codissolved in the same solvent. However, separate solvent streams of the olefinic compound and the initiator may be introduced into the hypophosphite solution so long as the introduction is substantially simultaneous. Once the organic compound and the free radical initiator have been introduced into the heated hypophosphite solution the temperature of the reaction mixture, the combined solutions, is maintained at or about the pre-selected temperature for a period of time effective to complete the reaction. For example, when a peroxyester is employed to initiate the reaction of a terminal olefin unsaturated ester or cycloalkene with sodium hypophosphite the typical reaction time will be within the range of about 1.5 to 6 hours, preferably about 2 to 5 hours. At the end of this reaction time the phosphinate salt is isolated simply by evaporating the solvents and drying the resulting solid salt in vacuo. The extent of reaction between the hypophosphite and the olefinic material to form the phosphinate is easily determinable by $^{31}$P NMR. Surprisingly it has been found that longer reaction times equivalent to those used in the prior art, for example 40 to 50 hours, do not result in increased yields but result in loss of reaction product. The use of the preferred reaction times in the present method typically provides yields of phosphinate salts on the order of 80 to 100%. These yields are attained at reaction times which are one or two orders of magnitude less than those taught to be optimal by the prior art.

The present invention will be further illustrated by reference to the following detailed examples.

EXAMPLE ONE

A solution of 224.4 gm Gulfteen 8 (2.0 moles, 96% 1-octene) and 6.06 gm t-butyl peroxymaleic acid in 400 gm reagent alcohol (Curtin Matheson Scientific, 95% denatured alcohol, 5% isopropyl alcohol) was added dropwise over a period of 3 hours to a stirred solution containing 201.4 gm of sodium hypophosphite monohydrate (1.9 moles), 300 gm reagent alcohol and 100 ml distilled water. The temperature was maintained at 80°0 C. throughout the addition and pH monitored (5.60–6.30). Two hours after post-addition, the solution was evaporated in vacuo to afford 425 gm dried product. Percent conversion to sodium octyl-1-phosphinate based on $^{31}$P NMR was 93%.

EXAMPLE TWO

The reaction was conducted by the procedure of Example One replacing t-butyl peroxymaleic acid with t-butyl peroctoate. A single phase reaction mixture was obtained at the end of 5 hours. A white powder was isolated and identified by $^{31}$P NMR to be sodium octyl-1-phosphinate. Percent conversion was determined to be 98%.

EXAMPLE THREE

A solution of 224.4 gm Gulfteen 8 (2.0 moles) and 6.06 gm 2,2'-Azobis(2-methyl-propionitrile) (AIBN) in 400 gm reagent alcohol was added dropwise over a period of 3 hours to a solution containing 201.4 gm sodium hypophosphite monohydrate (1.9 moles), 300 gm reagent alcohol and 100 ml distilled water. The temperature was maintained at 78° C.–80° C. and pH monitored (6.20–7.10). Three hours after post-addition, the solution was stripped to recover 63% yield of sodium octyl-1-phosphinate as confirmed by $^{31}$P NMR.

EXAMPLE FOUR

A solution of 224.4 gm Gulfteen 8 (2.0 moles) and 6.06 gm t-butyl perbenzoate was added dropwise over a period of 3 hours to a solution containing 201.4 gm sodium hypophosphite monohydrate (1.9 moles), 300 gm reagent alcohol and 100 ml distilled water. The temperature was maintained at 78° C. Forty five hours after post-addition, the system exhibited two phases. The bottom layer was separated and evaporated to yield 56% sodium octyl-1-phosphinate as indicated by $^{31}$P NMR.

EXAMPLE FIVE

A solution of 168.00 gm 1-hexene (Aldrich Chemical Co.), 400.00 gm reagent alcohol and 8.00 gm t-butyl peroxyneodecanoate (Lupersol 10 M-75, Pennwalt Chemicals) was added dropwise over a period of three hours to a solution containing 201.4 gm sodium hypophosphite monohydrate (1.90 moles), 266.0 gm reagent alcohol and 134.0 ml distilled water. The temperature was maintained at 78° C. Two hours after post-addition, the resulting clear solution was evaporated to yield 92% (by wt.) of sodium hexyl phosphinate.

EXAMPLE SIX

A solution of 82.15 gm cyclohexene (1.00 mole, Aldrich Chemical Co.) and 4.00 gm t-butyl peroxyneodecanate (Lupersol 10 M-75) in 200.00 gm reagent alcohol were added dropwise over a period of 3 hours into a solution containing 100.70 gm sodium hypophosphite (0.95 moles), 133.0 gm reagent alcohol and 67.0 ml distilled water. The temperature was maintained at 72°–74° C. Two hours after post-addition, the clear solution was evaporated to yield 80% (by wt.) of sodium cycohexylphosphinate.

EXAMPLE SEVEN

A solution of 280.00 gm 1-decene (2.0 moles, Aldrich Chemical Co.) and 6.06 gm t-butyl peroctoate in 400 gm reagent alcohol was added dropwise over a period of 3 hours to a solution containing 201.4 gm sodium hypophosphite monohydrate (1.90 moles), 300 gm reagent alcohol and 100 ml distilled water. The resulting solution was processed up as described in Example One to afford 92% (by wt.) of sodium decyl phosphinate.

EXAMPLE EIGHT

The reaction was conducted by the same procedure as described in Example Seven, replacing 1-decene with 1-dodecene (Gulfteen-12, 2.0 moles). The milky solution was processed to afford 94% (by weight) of sodium dodecylphosphinate.

EXAMPLE NINE

A solution of 415.60 gm of a mixture of 1-tetradecene and 1-hexadecene (Neodene C14–16, Shell Chem. Co.) (2.0 moles) and 6.06 gm t-butyl peroctoate in 650 gm reagent alcohol was added dropwise to a mixture comprising 201.4 gm sodium hypophosphite monohydrate (1.90 moles), 300 gm reagent alcohol and 100 ml distilled water. A temperature of 80° C. was maintained for 4 hours. The reaction mixture was dried in vacuo to recover greater than 90% (by wt.) of the corresponding sodium alkyl phosphinate.

EXAMPLE TEN

A solution of 63.5 Neodene 18 (94.7% octadecene, 0.25 moles) (Shell Chem. Co.) and 1.5 gm t-butyl peroctoate in 650 gm reagent alcohol was added dropwise to a mixture comprising 25.17 gm sodium hypophosphite monohydrate (0.2375 moles), 25 ml distilled water and 50 gm reagent alcohol. A temperature of 80° C. was maintained for about 5 hours. The reaction mixture was vacuum-evaporated to recover more than 90% (by wt.) of sodium octadecyl phosphinate.

EXAMPLE ELEVEN

A solution of 28.12 gm Neodene 20 (95% 1-eicosene, 0.10 mole) (Shell Chemical Co.) and 1.50 gm t-butyl peroctoate in 700 gm reagent alcohol was added dropwise to a mixture of 10.07 gm sodium hypophosphite monohydrate (0.095 mole), 30 gm reagent alcohol and 10 ml distilled water. A temperature of 78° C. was maintained for 5 hours. The reaction mixture was vacuum-dried to recover an almost quantitative yield of sodium eicosyl phosphinate.

EXAMPLE TWELVE

A solution of 75 gm dimethyl maleate (0.5 mole) and 2.0 gm t-butyl peroctoate in 100 gm reagent alcohol was added dropwise into a solution containing 53.0 gm sodium hypophosphite monohydrate (0.50 moles), 100 gm reagent alcohol and 50 ml distilled water. The temperature was maintained at 80° C. over a period of 4.5 hours. The reaction mixture was then evaporated in vacuo to afford almost quantitative yield of sodium 2-phosphinosuccinic acid dimethyl ester.

The above reaction method can be used to increase the rate and improve the yield of the free radical-catalyzed reaction between a wide variety of olefinic materials and hypophosphites, yielding highly active alkyl phosphinates which are easily isolated and purified.

EXAMPLE THIRTEEN

The ability of three of the phosphinate prepared by the procedures of Exs. 1, 5 and 6 supra, to chelate with calcium ion and to prevent its precipitation from aqueous solution as calcium carbonate was determined.

The calcium chelation values of the phosphinates prepared according to the present invention were determined visually by the following procedure. A microscopic stage illuminator lamp was set so that the beam would pass through a 1500 ml beaker at right angles to the analyst's line of sight. One liter of distilled water was introduced into the beaker and the phosphinate or phosphonate was dissolved in the water. The pH of the solution was measured and adjusted to pH 7 if necessary with 1N sodium hydroxide. Sodium carbonate (1 gram) was added to the solution and the solution pH was adjusted to pH 11 with sodium hydroxide. The phosphonate or phosphinate solution was then titrated with 0.25N calcium acetate solution by adding the calcium acetate solution dropwise and allowing each drop to fully react before adding the next drop. The end point was reached and the titration discontinued when the Tyndall effect was observed by the analyst at along at least two-thirds of the light beam. The chelation value was calculated by the following formula:

$$\text{Chelation Value (mgCaCO}_3\text{/gm)} = \frac{(\text{ml} - \text{OAc})(0.25)}{(\text{dry wt. sample})(0.01)}$$

In the above formula (dry weight) refers to the dry weight of the phosphinate or phosphonate which was titrated. The results of the titration of five sample weights of sodium octyl phosphonate and three phosphinates prepared according to the method of the present invention are summarized in Table I below:

TABLE I

| | Chelation Values* | | | | |
|---|---|---|---|---|---|
| | Weight of Chelator in Solution (g) | | | | |
| Chelator | 0.1 | 0.2 | 0.4 | 0.8 | 1.0 |
| Sodium Octyl Phosphonate | 1058 | 650 | 64 | 18.75 | 9.71 |
| Sodium Octyl Phosphinate | 1723 | 886 | 441 | 192 | 150 |
| Sodium Hexyl Phosphinate | 1538 | 780 | 356 | — | 149 |
| Sodium Cyclohexyl Phosphinate | 1568 | 723 | 350 | — | 150 |

*Values in mg CaCO$_3$/g of Chelator.

From the chelation values listed on Table I it can be seen that for an equivalent weight of chelator in aqueous solution the three phosphinates were substantially more effective in inhibiting the precipitation of calcium carbonate from solution than was sodium octyl phosphonate. For both the phosphonate and the phosphinates the efficiency of the calcium ion chelation affect decreased as the weight of the chelator increased. However, the loss in chelation efficiency per gram for sodium octyl phosphinate was observed to be approximately ten times greater than the loss of chelation efficiency observed for sodium octyl phosphonate.

The results summarized on Table I indicate that alkyl phosphinate salts prepared according to the method of the present invention will be highly effective to complex hardness factors such as calcium and magnesium cations. Thus it is expected that alkyl phosphinates which are water soluble, e.g. those containing less than about ten carbon atoms in the alkyl moiety, will be useful as builders in commercial and consumer detergent products. When used in such formulations, the present alkali metal phosphinate salts will act to inhibit or prevent the precipitation of inorganic and organic detergent components including builders such as sodium carbonate, sodium tripolyphosphate, sodium bicarbonate, sodium silicate, and the synthetic or natural alkali metal soap or nonsoap detergents.

Although the present invention has been described by reference to certain preferred embodiments, those with skill in the art will recognize that many modifications may be made therein without departing from the spirit and scope of this invention.

What is claimed is:

1. A method for the preparation of alkyl phosphinate salts by the reaction of an olefinic material with an alkali metal hypophosphite in the presence of an organic peroxyester free radical source comprising:
   (a) simultaneously adding an alcoholic solution of the olefinic material and an alcoholic solution containing essentially all of the free radical source or a mixture thereof to a reaction medium comprising an aqueous alcoholic solution of the hypophosphite, while maintaining the hypophosphite solution at about 50°–100° C. during the addition; and
   (b) heating the combined solutions at 50°–100° C. for about 1.5–6.0 hours to afford about an 80–100% yield of the alkyl phosphinate salt.

2. The method of claim 1 wherein the free radical source is an alkyl ester of a peroxycarboxylic acid or an alkyl ester of a monoperoxydicarboxylic acid.

3. The method of claim 1 wherein the reaction medium and the solution comprise ethanol.

4. The method of claim 3 wherein the reaction medium comprises about a 3:1 mixture of ethanol and water.

5. The method of claim 1 wherein the olefin is an alpha-olefin and the hypophosphite is sodium hypophosphite monohydrate.

6. The method of claim 1 wherein the olefin is an olefinic dicarboxylic acid or ester.

7. The method of claim 1 wherein the ratio of ethanol to water in the combined solutions is about 2–8:1.

8. The method of claim 1 wherein the combined solutions are heated at 50°–100° C. for 3–6 hours.

9. The method of claim 1 wherein the olefinic material is a $C_6$–$C_{22}$-alpha-olefin or a $C_5$–$C_8$-cycloalkene.

10. The method of claim 1 wherein the mole ratio of olefinic material to hypophosphite is about 1:1.

* * * * *

UNITED STATES PATENT AND TRADEMARK OFFICE
CERTIFICATE OF CORRECTION

PATENT NO. : 4,590,014
DATED : May 20, 1986
INVENTOR(S) : Stephen F. Wolf et al.

It is certified that error appears in the above-identified patent and that said Letters Patent is hereby corrected as shown below:

At Column 5, lines 32-33, for "80° OC" read --80°C--.

At Column 6, line 27, for "cycohexylphosphinate" read
     --cyclohexylphosphinate--.

At Column 6, line 57, for "phosphinate" read --phosphinates--.

At Column 7, line 28, for "phosphinate" read --phosphinates--.

At Column 7, line 53, for "(ml - OAc)" read --(ml ⁻OAc)--.

Signed and Sealed this

Thirtieth Day of September 1986

[SEAL]

*Attest:*

DONALD J. QUIGG

*Attesting Officer*  *Commissioner of Patents and Trademarks*